United States Patent [19]
Schram et al.

[11] Patent Number: 5,681,705
[45] Date of Patent: Oct. 28, 1997

[54] AMPLIFICATION AND DETECTION OF MYCOBACTERIUM AVIUM COMPLEX SPECIES

[76] Inventors: James L. Schram, 102 Dwelling Pl., Knightdale, N.C. 27545; James G. Nadeau, 710 Coker La., Chapel Hill, N.C. 27514; Cheryl H. Dean, 205 Trails End Ct., Raleigh, N.C. 27614

[21] Appl. No.: 520,194

[22] Filed: Aug. 28, 1995

[51] Int. Cl.$^6$ .............................. C12Q 1/68; C07H 21/04
[52] U.S. Cl. .............................. 435/6; 536/23.1; 536/24.3
[58] Field of Search ................... 435/6, 91.2; 536/22.1, 536/23.1, 24.3; 935/77, 78

[56] References Cited

U.S. PATENT DOCUMENTS 5,314,801  5/1994  Nycz et al. .

FOREIGN PATENT DOCUMENTS 6-133775  5/1994  Japan .

OTHER PUBLICATIONS

Uematsu et al., J. of the Japanese Assoc. for Infect. Dis. 67(5): 421–428 (1993). Abstract only Bej et al., Critical Reviews in Biochemistry and Molecular Biology 26 (3/4): 301–334(1991).

G. T. Walker, et al. "Isothermal in vitro amplification of DNA by a restriction enzyme/DNA polylmerase system" *Proc. Natl. Acad. Sci. USA* 89:392–396 (1992).

G. T. Walker, et al. "Strand displacement amplification—an isothermal, in vitro DNA amplification technique" *Nucl. Acids Res.* 20:1691–1696 (1992).

S. I. Takewaki, et al. "Nucleotide sequence comparison of the Mycobacterial dnaJ gene and PCR–restriction fragment length polymorphism analysis for identification of mycobacterial species" *Int. J. Syst. Bact.* 44:159–166 (1994).

S. I. Takewaki, et al. "Genus–specific Polymerase Chain Reaction for the Mycobacterial dnaJ gene and species–specific oligonucleotide probes" *J. Clin. Microbiol.* 31:446–450 (1993).

R. B. Lathigra, et al. "A gene from Mycobacterium tuberculosis which is homologous to the DnaJ heat shock protein of E. coli" *Nucl. Acids Res.* 16:1636 (1988).

*Primary Examiner*—W. Gary Jones
*Assistant Examiner*—Ethan Whisenant
*Attorney, Agent, or Firm*—Donna R. Fugit

[57] ABSTRACT

Amplification primers and methods are disclosed for complex-specific amplification of target sequences in the dnaJ genes of the *Mycobacterium Avium* Complex species. Also provided are assay probes for detection of the amplification products and/or identification of the MAC species which is present.

14 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_binding
        ( B ) LOCATION: 25..34
        ( D ) OTHER INFORMATION: /function= "target binding sequence"

( i x ) FEATURE:
        ( A ) NAME/KEY: misc_feature
        ( B ) LOCATION: 19..24
        ( D ) OTHER INFORMATION: /standard_name= "restriction endonuclease recognition site"

( x i ) SEQUENCE DESCRIPTION: SEQ ID NO:1:

TTGAACTCAC TCACTATTGT TGACCGGCGA ACGA    34

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_binding
        ( B ) LOCATION: 25..38
        ( D ) OTHER INFORMATION: /standard_name= "target binding sequence"

( i x ) FEATURE:
        ( A ) NAME/KEY: misc_feature
        ( B ) LOCATION: 19..24
        ( D ) OTHER INFORMATION: /standard_name= "restriction endonuclease recognition site"

( x i ) SEQUENCE DESCRIPTION: SEQ ID NO:2:

TTGAATAGTA GGATAGTAGT TGACAGGACA ACACGTTG    38

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_binding
        ( B ) LOCATION: 25..37
        ( D ) OTHER INFORMATION: /standard_name= "target binding sequence"

( i x ) FEATURE:
        ( A ) NAME/KEY: misc_feature (B) LOCATION: 19..24
(D) OTHER INFORMATION: /standard_name= "restriction endonuclease recognition sequence"

(xi) SEQUENCE DESCRIPTION: SEQ ID NO:3:

TTGAATAGTA GGATAGTAGT TGACCGACAA CACGTTG    37

(2) INFORMATION FOR SEQ ID NO:4:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

AGCTGGGCGT CTC    13

(2) INFORMATION FOR SEQ ID NO:5:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

GCGCTTGGCC G    11

(2) INFORMATION FOR SEQ ID NO:6:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

GACAATCCCG C    11

(2) INFORMATION FOR SEQ ID NO:7:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

GTGCGCCTCC GAC    13

(2) INFORMATION FOR SEQ ID NO:8:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

```
ACCGCCTTGA ATC                                                              13
```

(2) INFORMATION FOR SEQ ID NO:9:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ACGGCTTTGA ATC                                                              13
```

(2) INFORMATION FOR SEQ ID NO:10:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
GTGCGCCTCG GAG                                                              13
```

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
TTCAAGGCGG TCTCC                                                            15
```

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
TTCAAAGCCG TGTCG                                                            15
```

AMPLIFICATION AND DETECTION OF MYCOBACTERIUM AVIUM COMPLEX SPECIES

FIELD OF THE INVENTION

The present invention relates to amplification and detection of target nucleic acid sequences. In particular, the invention relates to amplification and detection of target nucleic acid sequences in Mycobacteria.

BACKGROUND OF THE INVENTION

The Mycobacteria are a genus of bacteria which are acid-fast, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum, M. paratuberculosis* and *M. tuberculosis*. Certain of these organisms are the causative agents of disease. For the first time since 1953, cases of mycobacterial infections are increasing in the United States. Although tuberculosis is of particular concern, other mycobacterial infections are also increasing as a result of an increase in the number of immune compromised patients. Many of these new cases are related to the AIDS epidemic, which provides an immune compromised population which is particularly susceptible to infection by Mycobacteria. *Mycobacterium avium, Mycobacterium kansasii* and other non-tuberculosis mycobacteria are found as opportunistic pathogens in HIV infected and other immune compromised patients.

*M. avium* and *M. intracellulare* are members of the *Mycobacterium avium* complex (MAC). These species have become important in recent years because of the high prevalence of disseminated MAC infection in AIDS patients. The *Mycobacterium avium* complex is comprised of 28 serovars which are distinguishable on the basis of their biochemical and seroagglutination characteristics (see review by Inderlied, et al. 1993. *Clin. Microbiol. Rev.* 6, 266–310). Depending on the method of classification, 10–12 of the 28 servors are classified as belonging to the species *Mycobacterium avium*, and 10–12 belong to the species *Mycobacterium intracellulare*. Six of the MAC serovars have not yet been definitively classified. MAC infections currently account for approximately 50% of the pathogenic isolates identified by mycobacteriology labs and are most common among AIDS and other immunocompromised patients. Early diagnosis and treatment of MAC infections can improve and prolong the lives of infected individuals.

At the present time the diagnosis of mycobacterial infections is dependent on acid-fast staining and cultivation of the organism, followed by biochemical assays. These procedures are time-consuming, and a typical diagnosis using conventional culture methods can take as long as six weeks. Automated culturing systems such as the BACTEC™ system (Becton Dickinson Microbiology Systems, Sparks, Md.) can decrease the time for diagnosis to one to two weeks. However, there is still a need to reduce the time required for diagnosing Mycobacterial infections to less than a week, preferably to about one day. Nucleic acid amplification is a powerful technology which allows rapid detection of specific target sequences. It is therefore a promising technology for rapid detection and identification of Mycobacteria. Examples of nucleic acid amplification technologies known in the art are Polymerase Chain Reaction (PCR: U.S. Pat. Nos. 4,683,195; 4,683,202; 4,800,159; 4,965,188), Strand Displacement Amplification (SDA) (G. Walker, et al. 1992. *Proc. Nat. Acad. Sci. USA* 89, 392–396; G. Walker, et al. 1992. *Nucl. Acids Res.* 20, 1691–1696; U.S. Pat. No. 5,270,184 which is hereby incorporated by reference), nucleic acid sequence based amplification (NASBA: U.S. Pat. No. 5,130,238 to Cangene), transcription based amplification (D. Kwoh, et al. 1989. *Proc. Nat. Acad. Sci. USA* 86, 1173–1177), self-sustained sequence replication (3SR: J. Guatelli, et al. 1990. *Proc. Nat. Acad. Sci. USA* 87, 1874–1878) and the Qβ replicase system (P. Lizardi, et al. 1988. *BioTechnology* 6, 1197–1202).

Isothermal amplification methods such as SDA and 3 SR have particular advantages in diagnostics, as they do not require the high/low temperature cycling characteristic of methods such as the PCR. They are therefore simpler protocols and require less specialized equipment to perform. However, for any nucleic acid amplification method a target sequence which can be amplified with the desired type and degree of specificity must be identified before the technology can be applied. The sequence of a selected target may not necessarily allow design of appropriate amplification primers for the selected amplification method and the target may not necessarily be amplified and detected with a degree of sensitivity and specificity suitable for diagnosis. European Patent Application 0 528 306 describes PCR amplification of a target sequence in the 16S ribosomal RNA gene of Mycobacteria using amplification primers directed to conserved regions of the gene. The amplification product, which is approximately 583 base-pairs in length, contains conserved sequence regions which hybridize to genus-specific probes and variable regions which can be used to identify species using species-specific probes. While the assay system described in EPO 0 528 306 is based on species non-specific amplification followed by species-specific detection of the amplification products, it is significant that the amplification product produced is very large. The larger the target sequence being amplified, the more likely it is that the amplification product will contain regions with sufficient sequence variation to allow the design of a variety of non-cross-hybridizing, species-specific probes for detection of amplification. Amplification methods such as SDA at this time are not capable of amplifying targets as large as those amplifiable by PCR. Small target sequences severely restrict the ability to design non-cross-hybridizing, species-specific probes for detection of a given target because there is less sequence available in the amplification product for assay probe design. Clearly, it is not certain whether amplification primers and assay probes with the desired specificity can be designed even when a target sequence is large. However, the problem of developing specific primers and probes is particularly acute when small target sequences are being amplified and detected. The problem is compounded when the selection of the target is further restricted by the requirement for sequences flanking a variable assay region which are not only close enough together for amplification but which also are highly conserved among the species of interest, thereby allowing species non-specific amplification of the assay region prior to species-, complex- or group-specific detection.

The heat shock proteins are a family of proteins which are expressed in elevated amounts when an organism is challenged by an increase in temperature. The heat shock proteins are highly conserved (R. J. Garcia, et al. 1989. *Infection and Immunity* 57, 204–212; R. S. Gupta, et al. 1992. *J. Bacteriology* 174, 4594–4605). The dnaJ gene codes for a 42 kd heat-shock protein believed to be involved in the cellular stress response. *M. tuberculosis* was the first of the mycobacteria for which the nucleotide sequence of the dnaJ gene was determined (R. B. Lathigra, et al. 1988. *Nucl. Acids Res.* 16, 1636). The nucleotide sequence of a segment of the dnaJ gene of *M. leprae* was subsequently determined (S. S. Harvey, et al. 1993. *J. Gen. Microbiol.* 139, 2003–2008). Later, using the *M. tuberculosis* sequence published by R. B. Lathigra et al., supra, S. I. Takewaki, et at. (1993. *J. Clin. Microbial.* 31, 446–450) developed a set of genus-specific PCR primers which amplify a 236-bp fragment of the dnaJ gene (bp 1394–1629) from a broad range of mycobacterial species, including *M. avium* and *M. intracellulare*. Species-specific oligonucleotide probes which allowed identification of *M. tuberculosis*, *M. avium*, *M. intracellulare*, and *M. kansasii* following genus-specific amplification by PCR were also reported. The dnaJ gene of nineteen species of mycobacteria was then sequenced and used to determine phylogenetic relationships and to differentiate species on the basis of species-specific restriction sites in the gene (S. I. Takewaki, et al. 1994. *Int. J. Syst. Bacteriol.* 44, 159–166). Japanese Kokai Patent No. 6-133775 (Takewaki, et al., published May 17, 1994) discloses a genus-specific amplification primer pair for PCR and several species-specific probes derived from the dnaJ gene of mycobacteria.

Certain terms used herein are defined as follows:

An amplification primer is a primer for amplification of a target sequence by extension of the primer after hybridization to the target sequence. For amplification by SDA, the amplification primers are preferably selected such that the GC content is low, preferably less than 70% of the total nucleotide composition of the probe, to minimize secondary structure. The 3' end of an SDA amplification primer (the target binding sequence) hybridizes at the 3' end of the target sequence. The target binding sequence confers target specificity on the amplification primer. The SDA amplification primer further comprises a recognition site for a restriction endonuclease near its 5' end. The recognition site is for a restriction endonuclease which will nick one strand of a DNA duplex when the recognition site is hemimodified, as described by G. Walker, et al. (1992. *PNAS*, supra). For the majority of the SDA reaction, the amplification primer is responsible for exponential amplification of the target sequence. The SDA amplification primer may also be referred to as the "S" primer (e.g., $S_1$ and $S_2$) when a pair of amplification primers is used for amplification of a double stranded sequence. For other amplification methods which do not require specialized sequences at the ends of the target, the amplification primer generally consists essentially of only the target binding sequence. For example, amplification of a target sequence according to the invention using the PCR will employ amplification primers consisting of the target binding sequences of the amplification primers in Table 1.

A bumper primer or external primer is a primer used to generate targets which can be amplified by SDA. The bumper primer anneals to a target sequence upstream of the amplification primer such that extension of the bumper primer displaces the downstream amplification primer and its extension product. Bumper primers may also be referred to as "B" primers (e.g., $B_1$ and $B_2$) when a pair of bumper primers is used to displace the extension products of a pair of amplification primers. Extension of bumper primers is one method for displacing the extension products of amplification primers, but heating is also suitable in certain amplification reactions.

The terms target or target sequence refer to nucleic acid sequences to be amplified. These include the original nucleic acid sequence to be amplified, the complementary second strand of the original nucleic acid sequence to be amplified, and either strand of a copy of the original sequence which is produced by the amplification reaction. These copies also serve as amplifiable target sequences by virtue of the fact that they comprise faithful copies of the original target sequences to which the amplification primers hybridize.

Copies of the target sequence which are generated during the amplification reaction are referred to as amplification products, amplimers or amplicons.

The term extension product refers to the single-stranded copy of a target sequence produced by hybridization of an amplification primer and extension of the amplification primer by polymerase using the target sequence as a template.

The term assay probe refers to any of the oligonucleotides used in the detection or identification portion of an assay. In the present invention, the assay probes are probes used for complex-, group- or species-specific detection or identification of Mycobacteria. Detector probes and capture probes are examples of assay probes.

The assay region or assay region sequence is the portion of a target sequence, or other nucleic acid, to which an assay probe hybridizes.

The term species-specific refers to detection or amplification in a species of organism without substantial detection or amplification in other species of the same genus or species of a different genus. Genus-specific refers to detection or amplification in the majority of the species of a genus, without substantial detection or amplification in the species of a different genus. Group- or complex-specific detection refers to detection or amplification in a majority of related species in a selected group (e.g., MAC) without substantial detection or amplification in other species of the same genus or species of a different genus.

SUMMARY OF THE INVENTION

The present invention provides oligonucleotide primers which may be used for complex-specific amplification of a target sequence found in 26 of the 28 serovars comprising the MAC. The target sequence is a segment of the dnaJ gene. Thus, a single pair of amplification primers enables amplification of 48 bp target sequences from the dnaJ gene of both *M. avium* and *M. intracellulare*. Oligonucleotide assay probes which hybridize to the assay region of the amplified target are used to detect the amplification products, optionally distinguishing between the MAC species. The inventive methods also allow detection of the dnaJ target sequence in *Mycobacterium paratuberculosis*, a subspecies of *M. avium* associated with Crohn's disease in humans and Johne's disease in livestock.

DETAILED DESCRIPTION OF THE INVENTION

Amplification primers which allow complex-specific amplification of a 48 bp target fragment of the dnaJ gene (bp 1548–1595) of MAC species are provided. The highly efficient amplification of targets in both *M. avium* and *M. intracellulare* was not predicted based on the sequence data of S. I. Takewaki, et al. (1994, supra), as the sequences of *M. avium* and *M. intracellulare* differ by a single nucleotide in the region where the amplification primers hybridize. Mismatches between the target binding sequences of primers and the sequences to which they hybridize in the target are generally known to inhibit or otherwise interfere with target amplification. In particular, the present invention provides oligonucleotide probes and primers which allow MAC-specific targets in the dnaJ gene to be amplified by Strand Displacement Amplification (SDA), with subsequent detection of the presence of a MAC species or identification of the particular MAC species which is present. It has been discovered that the primers of the invention produce $10^7$-fold amplification of both M. avium and M. intracellulare targets in spite of nucleotide sequence differences between these species at the site of amplification primer hybridization in the targets. In addition, following amplification, the amplified M avium and M. intracellulare target sequences may be distinguished from each other by hybridization to the assay probes of the invention.

The various probes and primers developed for SDA and detection of the MAC targets are shown in Table 1. The restriction endonuclease recognition sites (HincII) are bolded and the target binding sequences are italicized. The target binding sequence at the 3' end of each SDA primer determines its target specificity. The dnaJ sequences to which the amplification primers hybridize in M. avium and M. intracellulare differ by a single nucleotide at each end of the target. The amplification primers were therefore designed such that the target binding sequence of one of the primers hybridizes to one of the two targets (either M. avium or M. intracellulare) with perfect Watson-Crick complementary, but exhibits a single nucleotide mismatch when hybridized to the target in the other species. For example, the target binding sequence of SEQ ID NO: 1 hybridizes to the M. avium target with perfect complementarity but hybridizes to the M. intracellulare target with a single nucleotide mismatch. Similarly, the target binding sequence of SEQ ID NO:2 hybridizes to the M. intracellulare target with perfect complementarity but hybridizes to the M. avium target with a single nucleotide mismatch.

TABLE 1

Primers and Probes for Detection of dnaJ gene from MAC

| Function | Sequence |
|---|---|
| Amplification Primers | |
| Prim1 | 5'TTGAACTCACTCACTATTGTTGACCGGCGAACGA3' (SEQ ID NO:1) |
| IN2B | 5'TTGAATAGTAGGATAGTAGTTGACAGGACAAC-ACGTTG3' (SEQ ID NO:2) |
| Prim2 | 5'TTGAATAGTAGGATAGTAGTTGACCGACAACAC-GTTG3' (SEQ ID NO:3) |
| Bumper Primers | |
| BUMP1 | 5'AGCTGGGCGTCTC3' (SEQ ID NO:4) |
| BUMP2 | 5'GCGCTTGGCCG3' (SEQ ID NO: 5) |
| BUMP3 | 5'GACAATCCCGC3' (SEQ ID NO:6) |
| Capture Probes | |
| MAI33 | 3BIOTIN-5'GTGCGCCTCCGAC3' (M. intracelluare) (SEQ ID NO:7) |
| MAI37 | 5'ACCGCCTTGAATC3'-3BIOTIN (M. avium) (SEQ ID NO:8) |
| Detector Probes | |
| MAI36 | 5'ACGGCTTTGAATC3'-AP (M. intracellulare) (SEQ ID NO:9) |
| MAI38 | AP-5'GTGCGCCTCGGAG3' (M. avium) (SEQ ID NO:10) |
| DAV | 5'TTCAAGGCGGTCTCC3 (SEQ ID NO:11 |
| DIN | 5'TTCAAAGCCGTGTCG3' (SEQ ID NO:12) |

The presence of a single nucleotide mismatch destabilizes the primer-target complex as compared to a perfectly complementary complex, but, unexpectedly, does not appear to significantly reduce amplification efficiency under the reaction conditions of SDA. Initial hybridization of amplification and bumper primers to a target sequence in an SDA reaction results in generation of amplifiable targets as described by G. Walker, et at. (1992. Nucl. Acids Res., supra and U.S. Pat. No. 5,270,184). The target generation cascade produces copies of the desired target sequence flanked by nickable restriction endonuclease recognition sites. Therefore, during target-generation any single nucleotide mismatches between target and primer which were originally present are replaced by perfectly complementary sequences contributed by the amplification primers. These terminally-modified targets enter the amplification reaction and undergo SDA. Thus, the terminal sequences of the modified targets in both M. avium and M. intracellulare will become identical, but the assay regions between the sequences which bind the amplification primers will remain unchanged, allowing the amplification products of M. avium and M. intracellulare to be distinguished. Applicants hypothesize that this unique target generation feature coupled to SDA allows the amplification reaction to overcome the detrimental effects of primer/target mismatches as long as there is sufficient hybridization of the mismatched primer to the target to generate a single modified target suitable for amplification. This may account for the high efficiency of amplification observed in this system in spite of the mismatch. Using the amplification primers and bumper primers listed in Table I, the dnaJ targets of M. avium and M. intracellulare can be amplified >$10^7$-fold by SDA, permitting detection of as few as 5 copies of the target in M. avium and 50 copies of the target in M. intracellulare.

In Table 1, SEQ ID NO: 10 is a detector probe and SEQ ID NO:8 is a capture probe. Applicants found that cross-reactivity is detected if the functions of these two oligonucleotides are reversed, i.e., if SEQ ID NO:10 is used as the capture probe and SEQ ID NO:8 is used as the detector probe in the assay. However, cross-reactivity is eliminated by the probe configuration in Table 1, apparently because cross-reacting amplification products are not captured. Development of the inventive primers also illustrates that apparently minor modifications in amplification primers for SDA often have unpredictable effects, as deletion of the underlined A residue in SEQ ID NO:2 reduces the amplification efficiency in M. intracellulare by 100-fold and in M. avium by 10-fold. This result was unexpected in view of the fact that the underlined A residue is not part of the target binding sequence, but is part of an essentially randomly-selected sequence included to space the restriction endonuclease recognition site from the target binding sequence.

The amplification primers of the invention are also useful in other nucleic acid amplification protocols such as the PCR, thermophilic SDA (which uses heat-stable enzymes in a reaction scheme which is essentially the same as that of conventional low-temperature SDA) and 3SR. Specifically, any amplification protocol which utilizes cyclic, specific hybridization of primers to the target sequence, extension of the primers using the target sequence as a template and displacement of the extension products from the target sequence may employ the amplification primers of the invention. For amplification methods which do not require specialized, non-target binding sequences (e.g., PCR), the amplification primers may consist only of the target binding sequences of the amplification primers listed in Table 1. Amplification methods which require specialized, non-target binding sequences which are different than those of the amplification primers in Table 1 (e.g., 3SR) may employ amplification primers comprising the target binding sequences, with substitution of the sequence or structure required by the selected amplification method for the HincII site. Another restriction endonuclease recognition site appropriate for low-temperature SDA may also be substituted for the HincII site as is known in the art, or a restriction endonuclease recognition site appropriate for thermophilic SDA may be substituted when the target is amplified by thermophilic SDA.

The MAC species from which the amplification products are generated may be identified or distinguished by hybridization to the assay probes in the detection portion of the assay. For detection by hybridization, the detector probes are typically tagged with a detectable label. The detectable label is a moiety which can be detected either directly or indirectly as an indication of hybridization of the probe to the target nucleic acid. For direct detection of the label, probes may be tagged with a radioisotope and detected by autoradiography or tagged with a fluorescent moiety and detected by fluorescence as is known in the art. Alternatively, the probes may be indirectly detected by tagging with a label which requires additional reagents to render it detectable. Indirectly detectable labels include, for example, chemiluminescent agents, enzymes which produce visible reaction products and ligands (e.g., biotin, avidin, streptavidin, haptens, antibodies or antigens) which may be detected by binding to labeled specific binding partners (e.g., antibodies or antigens/haptens). Particularly useful labels include biotin (detectable by binding to labeled avidin or streptavidin) and enzymes such as horseradish peroxidase or alkaline phosphatase (detectable by addition of enzyme substrates to produce colored reaction products). Biotin and other ligands are also useful for tagging capture probes to allow immobilization of the capture probe and the complex to which it is hybridized on a solid phase by binding to the appropriate specific binding partner. Methods for adding such labels to, or including such labels in, oligonucleotides are well known in the art and any of these methods are suitable for use in the present invention.

One method for detecting amplification products employs polymerase extension of a primer specifically hybridized to the assay region. The primer is labeled as described above, e.g., with a radioisotope, so that the label is incorporated with the primer into an amplicon-specific extension product. Detection by primer extension is described by G. Walker, et al. (1992. Nuc. Acid Res. and PNAS, supra). A second method for detecting amplification products is a chemiluminescent assay in which amplified products are detected using a biotinylated oligonucleotide capture probe and an enzyme-conjugated oligonucleotide detector probe as described by C. A. Spargo, et al. (1993. Molec. Cell. Probes 7, 395-404). After hybridization of these two probes to different sites in the assay region, the complex is captured on a streptavidin-coated microwell plate, and the chemiluminescent signal is developed and read in a luminometer. The chemiluminescent assay can be performed in less than two hours and is sensitive enough to detect as few as one pre-amplification target sequence.

In one embodiment of the invention, the capture and detector probes shown in Table 1 can be used to detect the presence of M. avium and/or M. intracellulare amplification products. Because the assay regions of the amplification products in M. avium and M. intracellulare differ from each other at several nucleotide positions, the species may be distinguished using only the capture and/or detector probes specific for the assay region of the desired target. These same assay probes also detect M. paratuberculosis. Alternatively, the various assay probes may be combined in a single mixture for detecting the amplification products of all MAC species without distinguishing between them.

EXAMPLE 1

To determine the sensitivity of SDA for Mycobacterium avium and Mycobacterium intracellulare using the primers of the invention, target DNA was titrated and amplified. Genomic DNA isolated from these two species was prepared at concentrations of 10,000, 1000, 100, 10 and zero genomes with 50 ng of human placental DNA. SDA was performed essentially as described by G. Walker, et al. (1992. Nucl. Acids Res., supra), in a reaction buffer having the following composition: 45 mM potassium phosphate pH 7.6, 100 µg/ml acylated bovine serum albumin, 0.5 mM dUTP, 0.2 mM each dGTP, dCTP and alpha thio-dATP (dATPαS), 6 mM magnesium acetate, 7.5% dimethyl sulfoxide, and 5% glycerol. The dUTP was included to facilitate degradation of any contaminating amplicons (decontamination) with uracil-N-glycosylase (UNG). Amplification primers SEQ ID NO:1 and SEQ ID NO:2 were present in the reaction at a final concentration of 0.5 µM and bumper primers SEQ ID NO:5 and SEQ ID NO:6 were present at a final concentration of 0.05 µM. Target DNA was added and initially denatured (95° C., 2 min.), then cooled to 39° C. and decontaminated by addition of LING (0.5 units/reaction, incubate 30 min.). An internal control sequence was also included in each sample to monitor the amplification reaction. After decontamination, the UNG inhibitor Ugi (uracil N-glycosylase inhibitor) was added to stop the decontamination reaction. The enzymes, magnesium acetate and glycerol were also added. The restriction endonuclease HincII was used at a concentration of 150 units per reaction and exo⁻ Klenow polymerase was used at a final concentration of 3.6 units per reaction. SDA was conducted for 2 hr. at 39° C., and the amplification reaction was stopped by heating for 3 min. at 95° C.

The amplification products were detected in the chemiluminescence assay of C. A. Spargo, et al., supra. Alkaline phosphatase labeled detector probes, SEQ ID NO:9 and SEQ ID NO: 10 were added to the microtiter wells with the capture probes, SEQ ID NO:7 and SEQ ID NO:8. This mixture was incubated for 45 min. at 37° C. After incubation, the microtiter wells were washed three times with the stringency wash buffer (300 µl per wash). LUMI-PHOS 530 (Lumigen, Inc.) was then added to the wells and incubated for 30 min. at 37° C. Luminescence was detected using a luminometer (LUMISCAN, Labsystems) and relative light units (RLU) were recorded. The results are shown in Table 2:

TABLE 2

| SPECIES | GENOMES/REACTION | RLU |
| --- | --- | --- |
| M. avium | 10000 | 45049 |
|  | 1000 | 31417 |
|  | 100 | 9656 |
|  | 10 | 3082 |
| M. intracellulare | 10000 | 46847 |
|  | 1000 | 22048 |
|  | 100 | 3480 |
|  | 10 | 20 |
|  | 0 | 25 |

The results demonstrate a sensitivity of 10 genomes for M. avium and a sensitivity of 100 genomes for M. intracellulare.

EXAMPLE 2

To determine the specificity of the primers for M. avium and M. intracellulare, genomic DNA from various mycobacteria and non-mycobacteria species (listed in Table 3) was used as a target in SDA. The amplification reaction was conducted as described in Example 1, except that internal control sequences were not included and the reactions were not decontaminated. The results are shown in Table 3:

TABLE 3

| GENUS\SPECIES | GENOMES\REACTION | RLU |
|---|---|---|
| Mycobacterium africanum | 500000 | 38 |
| Mycobacterium avium | 100 | 2796 |
| Mycobacterium bovis | 500000 | 43 |
| Mycobacterium bovis BCG | 500000 | 118 |
| Mycobacterium chelonae | 500000 | 32 |
| Mycobacterium fortuitum | 500000 | 39 |
| Mycobacterium gordonae | 500000 | 192 |
| Mycobacterium intracellulare | 100 | 292 |
| Mycobacterium kansasii | 500000 | 45 |
| Mycobacterium paratuberculosis | 500000 | 77615 |
| Mycobacterium tuberculosis | 500000 | 93 |
| Mycobacterium xenopi | 500000 | 33 |
| Mycobacterium terrae | 500000 | 109 |
| Mycobacterium szulgai | 500000 | 15 |
| Mycobacterium marinum | 500000 | 24 |
| Mycobacterium gastri | 500000 | 60 |
| Mycobacterium haemophilum | 500000 | 92 |
| Mycobacterium malmoense | 500000 | 383 |
| Mycobacterium flavescens | 500000 | 103 |
| Mycobacterium genovense | 500000 | 110 |
| Corynebacterium diphtheriae | 500000 | 18 |
| Nocardia asteriodes | 500000 | 25 |
| Nocardia braziliensis | 500000 | 71 |
| Proprioniumbacterium acnes | 500000 | 10 |
| Rhodococcus eoui | 500000 | 19 |
| Streptomyces albus | 500000 | 32 |

The results show no significant amplification in species other than the MAC. Amplification in *M. paratuberculosis* is consistent, as this organism is considered a subspecies of *M. avium*. In most cases, the *M. intracellulare* and *M. avium* signals are similar in intensity. However, in this example, the *M. intracellulare* target gave a low but readily detectable positive signal. The *M. malmoense* signal detected in this experiment is believed to be an artifact of the high copy number of the target, and would be negative at copy numbers comparable to the MAC species samples.

EXAMPLE 3

The specificity of amplification was determined using cell lysates from 28 serovars of *M. avium* and *M. intracellulare*. SDA was performed as described in Example 1 except for omission of decontamination and the internal control sequence. Approximately 20,000 genomic targets of each serovar were tested for amplification, except for serovars 2 and 16 (100 genomes tested). The results are shown in Table 4:

TABLE 4

| SEROVAR | RLU | SEROVAR | RLU |
|---|---|---|---|
| 1A | 35536 | 13 | 3509 |
| 1B | 23534 | 14 | 12751 |
| 2 | 12271 (100 GENOMES) | 15 | 4280 |
| 2B | 13646 | 16 | 10029 (100 GENOMES) |
| 3 | 39213 | 17 | 18737 |
| 4A | 42663 | 18 | 75 (NEGATIVE) |
| 4B | 10564 | 19 | 975 (WEAK POSITIVE) |
| 5 | 32975 | 20 | 21150 |
| 6 | 32427 | 21 | 35691 |
| 7A | 479 (WEAK POSITIVE) | 22 | 30 (NEGATIVE) |
| 7B | 11705 | 23 | 67201 |
| 8 | 11155 | 24 | 39853 |
| 9 | 25123 | 25 | 2942 |
| 10A | 17964 | 26 | 2978 |
| 10B | 34342 | 27 | 29329 |
| 11 | 13113 | 28 | 833 (WEAK POSITIVE) |
| 12 | 2785 | | |

Twenty-six of the twenty-eight serovars were successfully amplified and detected using the primers and probes of the invention. Serovars 7A, 19 and 28 were weakly positive, but readily detectable. Serovars 18 and 22 did not amplify, but represent only a few percent of the serovars found in clinical samples. The eight serovars which represent approximately 90% of positive clinical samples were readily detected.

EXAMPLE 4

The dnaJ target sequence was amplified in *M. avium* and *M. intracellulare* using SEQ ID NO:1 and SEQ ID NO:3 as amplification primers. SEQ ID NO:4 and SEQ ID NO:5 were the bumper primers. The SDA reactions were performed essentially as described in Example 1, with either 0 or 20,000 copies of *M. avium* or *M. intracellulare* genomic DNA. For purposes of comparison, SEQ ID NO:3 was replaced with SEQ ID NO:2 in some reactions. The terminated reaction mixtures were assayed for the presence of amplification products specific for the dnaJ target fragment of either species using detector probe SEQ ID NO: 11 for *M. avium* and detector probe SEQ ID NO: 12 for *M. intracellulare* in a primer extension assay. To perform the assay, a 10 μL aliquot of the terminated reaction mixture was combined with 24 μL of a mixture containing 35 mM TRIS-HCl (pH 8.0), 7 mM $MgCl_2$, 350 μM each dCTP, dGTP, dTTP and dATPαS, and 1.65 pmoles of 5'-$^{32}$P labeled detector probe. The mixtures were heated to 95° C. for 2 min. and then placed in a 37° C. water bath. After 3–5 min., 1 unit of exo⁻ Klenow in 3 μL $H_2O$ was added to each sample and the mixtures were incubated at 37° C. for 20 min. The extension reactions were terminated by addition of 40 μL of 50% urea and 0.5X TBE. After heating at 95° C. for 2 min., 10 μL aliquots were analyzed by denaturing gel electrophoresis on a 10% polyacrylamide gel and autoradiography.

The results showed that SEQ ID NO: 1 and SEQ ID NO:3 amplified the target in both species. However, the *M. avium* target was amplified at least 50-fold more efficiently by this amplification primer pair than was the *M. intracellulare* target. The target binding sequences of SEQ ID NO: 1 and SEQ ID NO:3 form perfect duplexes when hybridized to the *M. avium* target but contain single nucleotide mismatches when either primer is hybridized to the *M. intracellulare* target. This may account for the less efficient amplification of the *M. intracellulare* target. When SEQ ID NO:3 is replaced by SEQ ID NO:2, amplification efficiency is increased about 10-fold. This may be due to the fact that the target binding sequence of SEQ ID NO:2 hybridizes to the *M. intracellulare* target with perfect complementarity. Unexpectedly, however, the substitution of SEQ ID NO:2 does not reduce the efficiency of target amplification in *M. avium* in spite of the introduction of a single nucleotide mismatch when this primer is hybridized to the *M. avium* target.

What is claimed is:

1. An amplification primer consisting of a target binding sequence selected from the group consisting of nucleotides 25–34 of SEQ ID NO:1, nucleotides 25–38 of SEQ ID NO:2 and nucleotides 25–37 of SEQ ID NO:3, and, optionally, a non-target binding sequence required by a selected amplification method.

2. The amplification primer of claim 1 selected from the group consisting of SEQ ID NO:1, SEQ ID NO:2 and SEQ ID NO:3.

3. A method for complex-specific amplification of a target nucleic acid of the *Mycobacterium avium* complex comprising:

a) hybridizing to the target nucleic acid a first amplification primer consisting of the target binding sequence of SEQ ID NO:1, and, optionally a non-target binding sequence required by a selected amplification method;

b) hybridizing to the target nucleic acid a second amplification primer consisting of the target binding sequence of SEQ ID NO:2 or the target binding sequence of SEQ ID NO:3, and, optionally the non-target binding sequence required by the selected amplification method, and;

c) amplifying the target nucleic acid in an amplification reaction in which the hybridized first and second amplification primers are extended on the target nucleic acid.

4. The method of claim 3 further comprising detecting the amplified target nucleic acid by hybridization to a detector probe consisting of SEQ ID NO:9, SEQ ID NO:10, SEQ ID NO:11 or SEQ ID NO:12 tagged with a detectable label.

5. The method of claim 4 wherein the amplified target nucleic acid is captured for detection by hybridization to a capture probe consisting of SEQ ID NO:7 or SEQ ID NO:8 tagged with a ligand.

6. The method of claim 3 wherein the non-target binding sequence required by the selected amplification method is a recognition site for a restriction endonuclease which nicks the recognition site when the recognition site is hemimodified, and the target nucleic acid is amplified by Strand Displacement Amplification.

7. The method of claim 6 wherein the target binding sequence of the second amplification primer consists of the target binding sequence of SEQ ID NO:2 and the hybridized first and second amplification primers are displaced from the target nucleic acid by extension of a first bumper primer consisting of SEQ ID NO:5 and a second bumper primer consisting of SEQ ID NO:6.

8. The method of claim 6 wherein the target binding sequence of the second amplification primer consists of the target binding sequence of SEQ ID NO:3 and the hybridized first and second amplification primers are displaced from the target nucleic acid by extension of a first bumper primer consisting of SEQ ID NO:4 and a second bumper primer consisting of SEQ ID NO:5.

9. The method of claim 3 wherein the first amplification primer consists of the target binding sequence of SEQ ID NO:1 and the second amplification primer consists of the target binding sequence of SEQ ID NO:2 or the target binding sequence of SEQ ID NO:3, and the target nucleic acid is amplified by the Polymerase Chain Reaction.

10. A method for complex-specific amplification of a target nucleic acid of the *Mycobacterium avium* complex comprising:

a) hybridizing to the target nucleic acid a first amplification primer consisting of SEQ ID NO:1 and a second amplification primer consisting of SEQ ID NO:2 or SEQ ID NO:3, and;

b) amplifying the target nucleic acid by Strand Displacement Amplification.

11. The method of claim 10 further comprising detecting the amplified target nucleic acid by hybridization to a detector probe consisting of SEQ ID NO:9, SEQ ID NO:10, SEQ ID NO:11 or SEQ ID NO:12 tagged with a detectable label.

12. The method of claim 11 wherein the amplified target nucleic acid is captured for detection by hybridization to a capture probe consisting of SEQ ID NO:7 or SEQ ID NO:8 tagged with a ligand.

13. The method of claim 10 wherein the second amplification primer consists of SEQ ID NO:2 and the hybridized first and second amplification primers are displaced from the target nucleic acid by extension of a first bumper primer consisting of SEQ ID NO:5 and a second bumper primer consisting of SEQ ID NO:6.

14. The method of claim 10 wherein the second amplification primer consists of SEQ ID NO:3 and the hybridized first and second amplification primers are displaced from the target nucleic acid by extension of a first bumper primer consisting of SEQ ID NO:4 and a second bumper primer consisting of SEQ ID NO:5.

* * * * *